US006969693B2

(12) United States Patent
Sauvage et al.

(10) Patent No.: US 6,969,693 B2
(45) Date of Patent: Nov. 29, 2005

(54) IMMOBILISED IONIC LIQUIDS

(75) Inventors: Emmanuelle Sauvage, Sorel Moussel (FR); Michael H Valkenberg, Aachen (DE); Christovao P De Castro-Moreira, Valencia (ES); Wolfgang F Hoelderich, Frankenthal (DE)

(73) Assignee: Johnson Matthey PLC, London (GB)

( * ) Notice: Subject to any disclaimer, the term of this patent is extended or adjusted under 35 U.S.C. 154(b) by 0 days.

(21) Appl. No.: 10/138,511

(22) Filed: May 6, 2002

(65) Prior Publication Data
US 2002/0169071 A1 Nov. 14, 2002

Related U.S. Application Data

(63) Continuation of application No. PCT/GB00/04215, filed on Nov. 3, 2000.

(30) Foreign Application Priority Data
Nov. 5, 1999 (EP) .................................. 99203668
Nov. 12, 1999 (DE) ................................ 199 54 485

(51) Int. Cl.[7] ............................................. G01J 31/00
(52) U.S. Cl. ...................... 502/159; 502/162; 502/164; 502/167; 502/169
(58) Field of Search ............................. 502/167, 169, 502/162, 164, 159

(56) References Cited

U.S. PATENT DOCUMENTS

| | | | |
|---|---|---|---|
| 3,294,764 A | | 12/1966 | Pellon |
| 3,915,797 A | | 10/1975 | Ishimatsu et al. |
| 4,025,459 A | * | 5/1977 | Wristers ..................... 502/169 |
| 4,148,837 A | | 4/1979 | Benson, Jr. |
| 4,179,403 A | * | 12/1979 | Kim et al. ............... 252/431 C |
| 4,519,909 A | * | 5/1985 | Castro ..................... 210/500.2 |
| 4,613,491 A | | 9/1986 | Jung et al. |
| 5,017,541 A | * | 5/1991 | Schmidt et al. ............. 502/169 |
| 5,288,677 A | * | 2/1994 | Chung et al. ............... 502/152 |
| 5,587,439 A | * | 12/1996 | DiMaio ...................... 526/142 |
| 5,693,585 A | * | 12/1997 | Benazzi et al. ............. 502/231 |
| 5,731,101 A | | 3/1998 | Sherif et al. |
| 5,801,113 A | * | 9/1998 | Jejelowo et al. ............ 502/104 |
| 5,807,938 A | * | 9/1998 | Kaneko et al. ............. 526/160 |
| 6,096,678 A | * | 8/2000 | Ray et al. .................. 502/152 |
| 6,673,737 B2 | | 1/2004 | Mehnert et al. |

FOREIGN PATENT DOCUMENTS

| | | |
|---|---|---|
| DE | 28 46 044 | 4/1979 |
| DE | 42 35 798 A1 | 4/1994 |
| EP | 0 306 564 A1 | 3/1989 |
| EP | 0 526 654 A1 | 2/1993 |
| EP | 0 545 774 A1 | 6/1993 |
| EP | 0545774 | 6/1993 |
| EP | 0553009 | 7/1993 |
| EP | 0553009 | 6/1997 |
| WO | WO 95/21806 | 8/1995 |
| WO | WO 98/50153 | 11/1998 |
| WO | WO 99/03163 | 1/1999 |

OTHER PUBLICATIONS

Brunel, Daniel et al. "MCM-41 type silicas as supports for immobilized catalysts" Stud. Surf. Sci. Catal., vol. 97 (1995) 173-180.

Boon, Jeffrey et al. "Friedel-Crafts Reactions in Ambient-Temperature Molten Salts" *J. Org. Chem.*, vol. 51 (1986) 480-483.

Carlin, Richard et al. "Catalytic Immobilized Ionic Liquid Membranes" *Electrochemical Society Proceedings*, vol. 98-11 (1998) 180-186.

Jones, Christopher W. et al. "Organic-functionalized molecular sieves as shape-selective catalysts" *Nature*, vol. 393 (May 7, 1998) 52-54.

Carlin, Richard et al. "Ionic liquid-polymer gel catalytic membrane" *Chem. Commun.* (1997) 1345-1346.

Carlin, Richard et al. "Chapter 5: Chemistry and Speciation in Room-Temperature Chloroaluminate Molten Salts" from *Chemistry of Nonaqueous Solutions Current Progress*, ed. Mamantov et al., VCH Publishers, New York (1994) pp. 277-306.

J.S. Wilkes in P. Wesserscheid and T. Welton, "Ionic Liquids in Synthesis", Wiley-VCH Verlag, Weinheim 2003, ISBN 3-527-30515-7, page 1.

J.D. Holbrey et al in P. Wesserscheid and T. Welton, "Ionic Liquids in Synthesis", Wiley-VCH Verlag, Weinheim 2003, ISBN 3-527-30515-7, page 41.

T. Welton et al., "Room-Temperature Ionic Liquids for Synthesis and Catalysis", Chem. Rev. 99, 1999 American Chemical Society, pp. 2071-2083.

R. Bartlet et al., "Syntheses et Proprietes D'Halogenures D'Ammonium Quaternaire Itilisables Comme Electrolytes", Journal de Chemie Physique, 1984, pp. 349-354.

(Continued)

*Primary Examiner*—J. A. Lorengo
*Assistant Examiner*—J. Pasterczyk
(74) *Attorney, Agent, or Firm*—Mayer Brown Rowe & Maw LLP

(57) ABSTRACT

Ionic liquids are immobilized on a functionalized support which carries or contains one component of the ionic liquid, or a precursor to such a component. The ionic liquid may be immobilized via the anion by treating a support with an anion source, e.g., an inorganic halide, before the ionic liquid is applied or formed. Alternatively, the ionic liquid may be immobilized by having the cation covalently bound to the support, e.g., through silyl groups, or incorporated in the support by synthesizing the support in the presence of a suitable base. The immobilized ionic liquids are of use as catalysts, for example, for the Friedel-Crafts reaction, such as alkylation reaction.

69 Claims, No Drawings

OTHER PUBLICATIONS

S. Saito et al., "Complexes of Urea and Symmetrical Tetraalkylammonium Halides", J. Am. Chem. Soc. 88:22, 1966, pp. 5107-5112.

R.S. Shelton et al., "Non-Acylated Quaternary Ammonium Salts from Aliphatic Amines", J. Am. Chem. Soc., 68, 1946, pp. 753-755.

H.A. Strobel et al., "Dielectric Behavior of Solutions of Electrolytes in Solvents of Low Dielectric Constant. III. The Influence of Constitution on Dielectric Absorption", J. Chem. Phys., vol. 16, No. 6, 1948, pp. 817-826.

H.E. Weaver et al., "Properties of Electrolytic Solutions. XXXII. Conductance of Some Long Chain Salts in Ethylene Chloride and Nitrobenzene at $25°^1$", J. Am. Chem. Soc. 1948, vol. 70, pp. 1707-1709.

W. Kantlehner et al., "Herstellung von 1,1,2,3,3-pentasubtittuierten und 1,1,2,2,3,3-hexasubstutuierten Guanidiniumsalzen Sowie vor 1,1,2,3,3,-Pentaalkyguanidinen", Leibigs Ann. Chem. 1984, pp. 108-126.

F.W. Wehrli et al., "$^{13}$C-, $^{14}$H-kemresonanzspektroskopische Untersuchungen an m-/p-substituierten N-Methylpyrisiniumjodiden", Helvetica Chimica Acta, vol. 54, Nr. 18-19, 1971, pp. 229-243

M. Sorm et al., "The Effect of Polymeric and Model Imidazolium Halides on the Rate of Hydrolysis of 4-Acetoxy-3-Nitrobenzoic Acid", Collection Czechoslovak Chem. Comm. 1985, vol. 50, pp. 845-853.

H. Ohno et al., "Ion Conductive Characteristics of Ionic Liquids Prepared by Neutralization of Alkylimidazoles", Solid State Inoics 154-155, 2002, pp. 303-309.

C. Damas et al., "Synthesis and Behaviour Study of Amphiphilic Polyvinylimidazolium Salts in Aqueous Media: Effects of the Microdomains on a Biomolecular Reaction Involving Hydrophobic Reactants", Eur. Polym. J., vol. 30, No. 11, 1994, pp. 1215-1222.

S.W. Kantor et al., "Rearrangements of Benzyltrimethylammonium Ion and Related Quarternary Ammonium Ions by Sodium Amide Involving Migration into the Ring", J. Am. Chem. Soc., vol. 73, 1951, pp. 4122-4131.

J.A. Cella et al., "The Relation of Structure and Critical Concentration to the Bacterial Activity of Quarternary Ammonium Salts", J. Am. CHem. Soc. 1952, vol. 74, pp. 2061-2062.

J.E. Adderson et al., "The Effects of Sugars on the Temperature Dependence of the Critical Micelle Concentration of Cationic Surfactants", J. Pharm. Pharmac., vol. 24, 1972, pp. 130-137.

L. Horner et al., "Reduktiver Abbau Quartarer Ammoniumsalze an der Blei-Bzw Quecksilberkathode", Justus Liebigs Ann. Chem., vol. 646, 1961, pp. 49-64.

D.P. Stevenson et al., "Note on the Structure of the Gallium and Indium Trihalides", J. Am. Chem. Soc., vol. 64, 1942, pp. 2514-2514.

W.A. Henderson et al., "The Nucleophilicity of Phosphines", J. Am. Chem. Soc., vol. 82, 1960, pp. 5794-5800.

W.J. Baily et al., "Phosphorus Compounds. II. Synthesis of the Unsymmetrical Tertiary Phosphines[1,2]", J. Org. Chem., vol. 25, 1960, pp. 1996-2000.

D. Jerchel, "Uber Invertseifen, XI. Mittell: Phosphonium- und Arsoniumverbindugen", Chem. Ber., vol. 76, 1943, pp. 600-609.

K.A. Petrov et al., "Preparation of Onium Hydroxides", J. Gen. Chem. USSR, vol. 42, 1972, pp. 2462-2464.

P. Bonhote et al., "Hydrophobic, Highly Conductive Ambient-Temperature Molten Salts", Inorg. Chem. vol. 35, 1996, pp. 1168-1178.

K.J. Harlow, "Convenient and General Synthesis of Symmetrical N, $N^1$-Disubstituted Imidazolium Halides", Synthesis, 1996, pp. 697-698.

J.M.G. Cowie, "Chemie and Physik der Synthetischen Polymere", Ubersetzung der Englischen Originalausgabe, Vieweg & Sohn Verlagsgesellschaft mbH, Braunschweig. Weisbaden 1997, ISBN 3-528-06616-4, pp. 57-73.

Y. Chauvin et al., "Flussige 1,3-Dialkylimidazoliumsalze asl Losungsmittel fur die Katalyse in Zweiphasensystemen: durch Rhodiumkomplexe Katalysierte Hydierung, Isomerisierung und Hydroformylerung von Alkenen", Angew. Chem, vol, 107, 1995, pp. 2941-2943.

D.P. Cox et al., ""Anhydrous" Tetrabutylammonium Fluoride: A Mild but Highly Efficient Source of Nucleophilic Fluoride Ion", J. Org. Chem., vol. 49, 1984, pp. 3216-3219.

R. Bruckner, "Reaktionsmechanismen", Spektrum Alademischer Verleg mbH, Heidelberg 1996, ISBN 3-8274-0096-1, p. 95, pp. 217-219 and pp. 481-484.

Copy of Opposition filed in the corresponding European application with English translation.

* cited by examiner

IMMOBILISED IONIC LIQUIDS

This is a Continuation of International Application No. PCT/GB00/04215 filed 3 Nov. 2000, which designated the U.S.

The present application relates to immobilised ionic liquids, and the use of these substances as catalysts in organic synthesis, refinery chemistry and petrochemistry.

It has been known since the early 80's that salts consisting of large organic cations and large, usually inorganic, anions may exhibit very low melting points. The chemical and physical properties of such ionic liquids can be varied over an extremely wide range. Thus the melting point, solubility in various solvents, solvent properties of the pure ionic liquid, viscosity and Lewis acidity can be specifically changed by changes to the components or the molar ratio of the components. The use of these salts optionally referred to as "molten salts" or "ionic liquids" as catalysts was reported back in 1986 by Wilkes et. al. in J. Org. Chem., 186, 51, 480–483. Ionic liquids whose anionic part is formed by excess Lewis acid metal salt, such as aluminium chloride, have proved active catalysts for Lewis acid catalysed reactions such as Friedel-Crafts reactions.

The use of ionic liquids in Friedel-Crafts reactions, especially in alkylation reactions, for example in the preparation of linear alkylbenzenes, has been disclosed in U.S. Pat. No. 5,731,101 and WO 95/21806. The aluminium chloride still used in the industry in large quantities, in pure form or as a benzene complex referred to as "red oil", has to be disposed of in an increasingly costly way due to more stringent environmental measures. Finding a replacement for such catalyst systems is therefore important from the economic and ecological point of view.

The immobilisation of catalytically active liquids on solid supports is verified in the literature and art by a large number of examples. The background to this process is largely the desire to transfer the catalytic properties of a homogeneous catalyst to a heterogeneous catalyst by immobilisation. The advantages of immobilisation lie in simplified separation, recovery and regeneration of the catalyst, low product contamination and synergistic effects produced by the support.

Immobilised ionic liquids are known from EP-A-0 553 009 and U.S. Pat. No. 5,693,585. Both these references describe how a calcined support is impregnated with an ionic liquid consisting of aluminium chloride and an alkylated ammonium chloride or imidazolium chloride in order to prepare an immobilised ionic liquid. The immobilised ionic liquids are used as catalysts in alkylation reactions.

This method for the preparation of immobilised ionic liquids, however, has a number of significant disadvantages. These include the limited application of these methods. Only by using certain ionic liquids, predominantly the strong Lewis acids, does the formation of a covalent bond between the inorganic anion and the support material take place. In other cases, a solid bond of this type cannot be produced, therefore there is always the danger of leaching, i.e. a purging of the ionic liquid from the support. Furthermore, there is also the danger with acid, i.e. easier to immobilise, ionic liquids, that the structure of crystalline supports is attacked during immobilisation. Another disadvantage of immobilisation via the inorganic part of the ionic liquid is that due to bonding on the surface, some of the Lewis acid metal halides are only partly available for catalysis.

A completely different method of immobilisation was developed by Carlin et al in Chem. Comm., 1997, 1345–1346 and Proc.-Electrochem. Soc., 1998, 98–11, 180–186. Here an ionic liquid used as solvent for a nickel or palladium catalyst is dissolved in a perfluorinated polymer. A membrane in which the ionic liquid is immobilised is obtained by cooling the melt in a pan-type vessel. The recognisable disadvantage of this method is the high sensitivity to organic solvents and elevated temperatures. The melting point of the polymer is approx. 75° C.

The problem was to develop a catalyst system combining the various application possibilities of ionic liquids and the advantages of a heterogeneous catalyst. At the same time, the disadvantages of the methods known from the literature for the immobilisation of ionic liquids should be addressed by developing a method which, if possible, both allows the use of structured supports and also facilitates the immobilisation of weak Lewis acid metal halides.

We found that these problems were overcome by forming a functionalised support prior to formation of the ionic liquid, or prior to contact with the ionic liquid. This method allows the preparation of catalyst systems which, despite their immobilisation on a support material, exhibit in their composition the varied possibilities of pure ionic liquids.

According to the present invention immobilised ionic liquids having an anion component and an organic cation component are produced by first forming, in the absence of the ionic liquid, a functionalised support material containing, or bearing, a first compound which has, bonded to said support, a component that is one of anion and cation components of the ionic liquid, or a precursor to such a anion or cation component, and thereafter treating said functionalised support material with the ionic liquid or a composition which contains at least the other of the anion and cation components of the ionic liquid, or a precursor to the other of the anion and cation components.

Thus in the invention, a functionalised support is formed, in the absence of the ionic liquid, and then the functionalised support is contacted with the ionic liquid or the latter is formed from, or in the presence of, the functionalised support.

The ionic liquid can be any conventional ionic liquid. Typically, they are classified as fused salt compositions that are liquid at a temperature below the melting point of the individual components. Preferably, the melting point of the ionic liquids as used in the present invention is between −10° C. and 100° C., more preferably −10° C. and 60° C., and most preferably 0° C. to −30° C., all at atmospheric pressure.

Conventional ionic liquids are typically formed by combining an inorganic halide and an organic base. While other anion sources, e.g. inorganic or organic sulphonic acids, may be used, inorganic halides are preferred. Suitable halides are those compounds that can form anions containing polyatomic halide bridges in the presence of a hydrocarbyl containing amine hydrohalide salt. Preferably, the halides are covaiently bonded halides of metals of Groups 8 to 14 of the Periodic Table. Preferred metals are aluminium, boron, gallium, iron, copper, zinc, tin, and indium, with aluminium being most preferred. Examples of suitable metal halides include copper monochloride, ferric trichloride, zinc dichloride and aluminium trichloride.

Organic bases suitable for forming conventional ionic liquids include hydrocarbyl-containing amine hydrohalide salts, such as alkyl-containing amine hydrohalide salts based on trimethylamine, ethylenediamine, ethylenetriamine, morpholine, imidazole, guanidine, picoline, piperazine, pyridine, pyrazole, pyrrolidine, triazine, triazole, pyrimidine, derivatives of such molecules, and/or mixtures thereof, and phosphonium compounds.

As is known in the art, various ratios of inorganic halide to organic base can be used to make the conventional ionic liquids. Stoichiometric amounts of base and inorganic halide are defined such that a neutral ionic liquid is obtained. If the supported ionic liquid of the invention is to be used as a catalyst in subsequent alkylation reactions, the final ionic liquid is preferably acidic.

Ionic liquids that can be used in the process of the invention include chloroaluminates (such as the salts obtained by combining $AlCl_3$ and an organic base), chlorogallates (based on, e.g. $GaCl_3$) and mixed ionic liquids e.g. based on three or more ions, e.g. a cation and two or more anions, or an anion and two or more cations, e.g. ternary ionic liquids derived from $AlCl_3$ and (alkyl)imidazolium chloride and (alkyl)pyridinium chloride, or derived from $AlCl_3$ and a hydrocarbyl substituted quaternary ammonium halide and a hydrocarbyl-substituted phosphonium halide.

In one form of the invention the functionalised support is prepared by treating an oxidic support with the anion source, e.g. an inorganic halide, in an inert atmosphere in the absence of the ionic liquid and then the so treated support is contacted with an ionic liquid or components that react to form an ionic liquid. In this way the ionic liquid is immobilised via the anion.

In this way leaching of the ionic liquid from the support can be significantly reduced and also problems associated with a conventional impregnation route, namely the need to shield the support and ionic liquid from water, since any traces of water that are present during the Impregnation step will result in deterioration of the support, can be decreased.

In another form of the invention, the ionic liquid is immobilised via the cation, by forming a support containing the cation, or precursor thereto, or by treating a pre-formed support with a reagent containing the cation, or precursor thereto, so that the cation, or precursor thereto, is "grafted" to the support.

The formation of a functionalised oxidic support has been described by Jones et al. in Nature, 1998, 393, 52–54, and by Brunel et al. in Stud. Surf. Sci. Catal., 1995, 173–180. In these cases, however, an attempt was for the most part made to bond a catalyst successfully used in homogeneously catalysed reactions to the surface of a support, for the most part a molecular sieve or mesoporous material. In contrast, in the present invention, the organic molecule, however, is only part of the actually catalytically active component. Only by adding the inorganic component is an environment created which corresponds to covering the surface with an ionic liquid.

The support materials that can be used in the process according to the invention include microporous and mesoporous as well as macroporous supports. Hence the support may have an average pore diameter from 3 nm to 1 mm, as can be determined using conventional techniques. Preferably, the supports have a BET surface area of 0.1 to 1500 $m^2/g$, more preferably 100 to 1200 $m^2/g$.

Suitable and preferred supports are solid oxidic materials such as clays, silica, alumina, aluminosilicates, especially zeolites (such as zeolite Y as obtainable from Degussa or Zeolyst International), titanium oxide, boron oxide, or any other metal oxide containing hydroxyl groups on the surface. Such supports include the preferred MCM-types of materials that have a desirable high surface area and include mesoporous materials such as MCM 41, MCM 48 and HMS (hexagonal mesoporous sieve) materials. The process of the invention is most advantageous for making supported ionic liquids on a "regularly ordered" or "structured" support, hereinafter also called a nanosupport, such as zeolites and MCM-type materials. Such structured/ordered supports show sharp peaks in the XRD spectrum, as is known in the art.

Where the support is contacted with a water-sensitive material, such as $AlCl_3$, before, during or after forming the functionalised support, the support should be dry. Such dried supports can be obtained by any suitable technique, e.g. calcination, desiccation, and the like. Depending on the chemical structure of the support, calcining may be the preferred way of drying the support. Supports based on silica, alumina, aluminosilicate, such as zeolite and mesoporous materials of the MCM type, and the like, are preferably dried by calcination. The calcination temperature is not critical, and what temperatures can be applied will again depend on the chemical structure of the support. Typically, calcination is performed at temperatures in the range of 300 to 650° C., preferably 450 to 600° C., for 1 to 12 hours, preferably 1 to 6 hours, for example about 3 hours, in order to render supports suitable for use according to the invention. To keep the supports dry, they should be stored in an inert atmosphere.

In the first form of the invention, viz. immobilisation via the anion, the support is treated with an anion source, e.g. inorganic halide, which is preferably selected from the inorganic halides suitable for making an ionic liquid, to form the functionalised support which is then contacted, e.g. impregnated, with the ionic liquid or reagents that react to form the ionic liquid. For the pre-treatment, aluminium, boron, gallium, iron, copper, zinc, indium, and tin halides are preferred, particularly aluminium, iron, and tin halides. Preferred halides are the chlorides. Most preferred is aluminium trichloride.

The treatment step is typically conducted by stirring a slurry of support and a solution of the inorganic halide in a solvent such as dried methylene chloride for about an hour at room temperature (25° C.) in an inert atmosphere. The solvent, e.g. methylene chloride, can be dried in a conventional way, e.g. by distillation over $CaCl_2$. Other solvents and reaction conditions can be chosen, as will be clear to the skilled person. If $AlCl_3$ is used, for instance, it is known that protic solvents cannot be used. However, most solvents can be used if $SnCl_2$ is used in the pretreatment step. The amount of solvent to be used depends on the reaction conditions. Typically, the solvent is used in an amount that allows proper stirring of the mixture. After the treatment, the solvent can be removed or the solution can be used as is. Removed solvent can be recycled.

Depending on the support that is used, the ratio of inorganic halide to support in the pretreatment step needs to be optimized. Preferably, the halide reacts with the reactive groups, typically being hydroxyl groups, on the surface of the support. Therefore, the inorganic is preferably used in a more than stoichiometric amount, based on the amounts and types of reactive groups on said surface. For a dried Y-zeolite, 1 g of $FeCl_3$ was successfully used to treat 5 g of the zeolite. However the halide can be used in far greater amounts, especially if the same halide is subsequently used to make the ionic liquid in situ during a subsequent impregnation step.

The support is preferably dried prior to contact with the inorganic halide to avoid wasting inorganic halide through the formation of HCl. When using dried supports, the amount of inorganic halide needed to treat the support can be significantly reduced.

In a preferred embodiment of the invention, a support is first contacted with the inorganic halide to form the functionalised support which is subsequently impregnated with the ionic liquid. It should be understood that the term "impregnation" as used herein relates to any technique wherein an ionic liquid is absorbed in a support and/or an ionic liquid is adsorbed on the surface of said support. Typically, such impregnation simply means that the pretreated support and the ionic liquid are blended. However, the ionic liquid might be formed in situ during the impregnation step, meaning that the pretreated support is mixed with the chemicals to form the ionic liquid.

If desired, the pretreated support can be impregnated with the ionic liquid immediately after the pretreatment step, preferably in the same reactor. As explained below, the ionic liquid may be added in the ionic liquid form or may be formed in situ by adding the compounds forming such ionic liquid. Where the ionic liquid is added as such, it preferably contains less than the desired amount of inorganic halide in order to compensate for the amount of inorganic halide that is present in and on the treated support. Where the ionic liquid is formed in situ, at least 10%, and preferably all, of the inorganic halide used to form the ionic liquid may have been present already during the pretreatment step. Where all of the inorganic halide was present in the pre-treatment stage, just the addition of organic base is required during the impregnation step. Because this mode of operation allows for a high metal halide concentration in the pretreatment step with consequent shorter reaction times, this is the preferred way to conduct the process of the invention. However it is also feasible to first treat with a certain amount of an inorganic halide and to subsequently add, in any sequence, organic base and further inorganic halide. The inorganic halide so used to form the ionic liquid may or may not be the same compound as was used for the pretreatment.

The process steps should be performed in an inert atmosphere to prevent water from entering. Although the process according to the invention is less sensitive to water, in that the support is not destroyed if water is present in the pretreatment step, the water will react with the other chemicals used in the process, thereby wasting raw materials and resulting in the undesired formation of by-products. Preferably, nitrogen or argon is used to ensure an inert atmosphere, nitrogen being preferred. However, dried inert solvents can also be used.

The amount of ionic liquid used for impregnating the treated support will also depend on the support used and the amount of pretreatment agent on the support, as is explained in more detail below. Good results were obtained in processes where an excess of ionic liquid was used, in particular where the weight ratio of ionic liquid to support was chosen from 2:1 to 1:2. Preferably, so much ionic liquid is used that, after stirring for 0.5 hour, some unabsorbed ionic liquid can still be seen on the surface of the support. If an excess of ionic liquid is used, the excess is preferably removed to avoid leaching of ionic liquid upon use of the supported catalyst formed. Suitably the excess ionic liquid is removed by Soxhlet extraction with refluxing methylene chloride. The ionic liquid so removed can be reused for the impregnation of fresh support.

The impregnation can be conducted by stirring a mixture of the pretreated support and ionic liquid or by stirring a mixture of pretreated support and compounds capable of making an ionic liquid in situ. The stirring is preferably conducted above the melting temperature of the ionic liquid. Stirring for a period of at least three hours, preferably overnight, was found to suffice in most cases.

However, the skilled person will have no problem varying the impregnation conditions, if so desired. For instance, it is possible to use a solvent to improve the homogeneity of the supported ionic liquid.

When analysed by X-ray diffraction (XRD), the supported ionic liquids so obtained showed that after impregnation the support was still intact. Although we do not wish to be bound by the following theory, it is believed that the beneficial properties of the pretreatment step are due to the fact that the inorganic halide will react with reactive groups, particularly OH-groups, of oxidic supports with the formation of HCl. Preferably, the reaction results in a support to which the inorganic halide is covalently bonded. The HCl is liberated and will diffuse from the support before the ionic liquid is introduced.

If a conventional impregnation technique is used, i.e. without any pre-treatment to form a functionalised support in accordance with the present invention, the ionic liquid will react with the reactive groups of the support, with the formation of HCl. In this case, however, an ionic liquid is present and the HCl that is formed will have super-acidic properties, as is known in the art, see, for instance, "Chemistry of non-aqueous solutions: Current progress" Chapter 5 of R. T. Carlin, J. S. Wilkes, Ed. G. Mamantov, I. Popov, "Chemistry and Speciation in Chloroaluminate Molten Salts" Wiley-VCH, N.Y., 1994, pp. 277–306. Hence, conventional impregnation techniques are expected to result in the formation of super-acidic HCl whereas this is prevented in the process of the invention. In the case of structured/ordered supports, such as zeolites and MCM-type materials, super-acidic HCl typically was found to destroy the support material. Accordingly, conventional impregnation processes result in (partially) destroyed supports, while in the process according to the invention this is not the case, or at least is the case to a lesser extent. Furthermore, the inorganic halide now attached to the support, particularly when it is covalently bonded to the support, will become part of the ionic liquid when the ionic liquid is absorbed on and into the support. This, together with the fact that the structure of the support is not damaged, is believed to be the reason why the supported ionic liquid according to the invention shows less leaching of the ionic liquid than conventional supported ionic liquids do when used in subsequent processes.

In an alternative and preferred form of the invention, the ionic liquid is immobilised via an organic cation covalently bonded to the surface of the support. This has a number of advantages over the other methods described.

The functionalised support can be produced in different ways. One option is by reacting an organic compound having suitable reactive groups, such as (ethoxy-alkyl)-silyl groups, with the hydroxyl groups on the surface of the support. Solid covalent bonds are produced here as a result of a condensation reaction, with the corresponding alcohol splitting off. The use of appropriate organic compounds, such as (tri-ethoxy-silyl)-propyl-alkyl-imidazolium chloride, allows the cationic part of the ionic liquids to be applied to a support in large quantities without the structure of the support material being affected.

A second option is the specific incorporation of suitable organic molecules in, for example, amorphous silica or mesoporous materials of the MCM 41 type. An organic molecule can be incorporated into the support during the synthesis of the support material. Thus supports containing the organic bases needed for the ionic liquids can be synthesised by incorporating a suitable amine in the synthesis of the support.

In another option, a non-oxidic support is used. Thus the functionalised support may be a polymer which contain the required cations, e.g. as end groups, or which are provided with the corresponding functions by specific synthesis.

The inorganic halide can be added to the functionalised support containing or carrying the organic cation, or precursor thereto, in various ways. The type of addition depends on the halide used and the desired immobilised ionic liquid. For example, $AlCl_3$ in solution can be added to an imidazolium chloride immobilised on the support. Reaction with the chloride already present produces the chloroaluminate anion. Selection of the suitable solvent is dependant in each case on the halide used. The reaction conditions must also be selected as a function of the halide used; in general the reaction can take place at room temperature.

Should it not be possible to form the desired anion from a halide already present and a neutral metal halide by simple reaction, the anion can be introduced by an ion exchange. This is the case for example with tetrafluoroborate and hexafluorophosphate anions. Here a simple salt of the anion is added in a suitable solvent and passed over the functionalised support at room temperature until analysis confirms complete exchange of the anions. Selection of the solvent, analysis and conditions of the ion exchange may be specifically selected as a function of the salt used.

Preferred immobilised ionic liquids with the ionic liquid immobilised via the cation are those containing quaternary ammonium, imidazolium, or pyridinium groups, in which one or more of the carbon atoms may be substituted, covalently bonded to the support through a hydrocarbyl or silyl hydrocarbyl linkage containing up to 12 carbon atoms. The silyl group may be alkyl substituted, e.g. with alkyl radicals containing up to 6 carbon atoms. Preferred substituents for the carbon atoms of the quaternary ammonium, imidazolium, or pyridinium groups are alkyl radicals having 1 to 10 C atoms, e.g. methyl, ethyl, propyl, isopropyl, butyl, isobutyl, tert-butyl, pentyl, hexyl, octyl, decyl, cyclohexyl; alkenyl radicals having 1 to 10 C atoms, e.g. ethenyl, n-propenyl, isopropenyl, hexenyl, 3-methylpentenyl, 3-ethylbutenyl; aralkyl radicals, e.g. benzyl, 1-phenylethyl, 2-phenylethyl, 2-phenylpropyl, cumylmethyl, mesitylmethyl; and alkyloxy radicals containing 1 to 10 C atoms and possibly also containing phosphorus or sulphur as other hetero atoms, e.g. methoxy, ethoxy, propyloxy, butyloxy, 2-ethylbutyloxy, 3-thiabutyloxy and 3-phosphabutyloxy.

In the preferred ionic liquids immobilised via the cation, the anion is preferably a halide containing aluminium, antimony, gallium, iron, copper, zinc, indium, tin, boron or phosphorus.

The anions may also contain transition metal and/or noble metal complexes, for example complexes formed from rhodium, copper, nickel, cobalt, palladium or platinum and ligands which may contain, in addition to carbon and hydrogen, elements such as phosphorus nitrogen, oxygen or sulphur.

The catalyst systems obtained in accordance with the above description may be used in a large number of organic reactions, such as alkylation, acylation or carbonylation reactions, e.g. of aromatics or olefins; addition; elimination; nucleophilic substitution; oxidation or fluorination reactions.

Examples of such processes include, but are not limited to: the alkylation of aromatic compounds, such as benzene, naphthalene, phenanthrene, and the like, with olefins, such as ethylene, propylene, isobutene, decene, dodecene, and the like; the oligomerization of olefins, such as ethylene and propylene; the acylation of olefins and aromatic compounds with acid chlorides and/or anhydrides, such as acetyl chloride and acetic anhydride: carbonylation reactions, such as the reaction of phenol with carbon monoxide or the reaction of isobutene with carbon monoxide to form pivalic acid; and oxidation reactions, such as the process to produce benzoic acid from toluene; and other organic syntheses such as the Heck and Suzuki reactions.

The potential use of the immobilised ionic liquids as catalysts corresponds to the potential applications of the corresponding ionic liquids, with the advantage that the ionic liquid is less liable to leach from the supports than from immobilised ionic liquids prepared simply by impregnating a support that had not been functionalised with an ionic liquid. Hence, the supported ionic liquids of the invention have a longer catalyst life and lead to lower contamination of the product stream than conventional supported ionic liquids.

The reaction conditions can be varied over a wide range. With reactions in the liquid phase, the temperature limits are set by the melting and boiling points of the reactants or the solvent, if any, used. The reaction can be carried out batchwise or by a continuous reaction procedure. Should a solvent be needed, all normal solvents such as benzene, toluene, methylene chloride, diethyl ether and ethanol, as well as others, can be used. The only restriction is the possibility of a reaction of the inorganic anion with the solvent, as is the case for example for water and aluminium or iron chloride.

In the case of gas phase reactions, both fixed bed reactors and fluidised bed reactors or other types of reactor can be used. Often in the case of gas phase reactions, a carrier gas is used; any gas which does not react itself or as a result of impurities with the inorganic anion, can be used. The temperature may be between the boiling point of the reaction mixture used and 500° C., preferably between 100° C. and 350° C., particularly between 150 and 300° C.

Whilst the pressure is preferably atmospheric, this is not absolutely necessary; the procedure can be carried both at higher pressures and at partial vacuum. The catalyst load expressed by the WHSV can be varied in a range of 0.1 to 50 $h^{-1}$; a WHSV between 1 and 20 $h^{-1}$ is preferred. As with all other reaction conditions, this must be decided as a function of the reaction.

The invention is illustrated in greater detail in the following by the following examples in which all percentages are by weight.

EXAMPLE 1

7.9 g silica dried at 500° C. (FK 700, Degussa) was suspended in 50 ml toluene in a distillation apparatus and mixed whilst stirring with 4.9 g 1-(tri-ethoxy-silyl)-propyl-3-methyl-imidazolium chloride. After stirring for 16 h at 95° C., the solvent was distilled off at 135° C. The solid was then extracted in a Soxhlet apparatus for 24 h with boiling $CH_2Cl_2$ and then dried under vacuum to remove any excess 1-(tri-ethoxy-silyl)-propyl-3-methyl-imidazolium chloride.

The CHN analysis (N: 2.22%; C: 8.63%; H: 2.25%) corresponds to 0.8 mmol imidazolium chloride per g.

3.0 g of the resultant functionalised support was suspended at room temperature in 30 ml toluene in a Schlenk flask under a gas blanket. After adding 2.8 g $AlCl_3$, the mixture was stirred for 16 h, then the solvent was removed under vacuum. The excess $AlCl_3$ was then removed by 24 hour extraction with boiling $CH_2Cl_2$ to give the immobilised ionic liquid product.

The CHN analysis (N: 1.87%; C: 7.21%; H: 2.62%) corresponds to 0.7 mmol imidazolium chloride per g and analysis by inductive coupled plasma atom emission spectroscopy (ICP-AES) (Si: 25.89%; Al: 4.99%) corresponds to 1.9 mmol $AlCl_3$ per g.

3.52 ml (39 mmol) benzene was alkylated with 0.88 ml (3.9 mmol) dodecene using 0.29 g of the immobilised ionic liquid as catalyst by heating the mixture with stirring for 1 hour to 80° C. in a Schlenk flask with reflux condenser. A 92% dodecene conversion was achieved with a selectivity of 76% to the monoalkylated product.

EXAMPLE 2

A solution of 10 g $NaBF_4$ in 300 ml $H_2O$ is passed over 4.1 g of the remainder of the functionalised support of Example 1 in a protective gas frit. After approx. 24 h, the wash solution collected under the frit contained no more chloride ion. The solid was washed several times with distilled water and then dried under high vacuum.

The CHN analysis (N: 0.94%; C: 3.36%; H: 1.53%) of the resulting immobilised ionic liquid corresponds to 0.34 mmol imidazolium chloride per g and analysis by ICP-AES (Si: 39.93%; B: 0.12%) corresponds to 0.1 mmol $BF_3$ per g.

EXAMPLE 3

3.4 g of all-silica MCM 41 calcined at 500° C. was suspended in 50 ml toluene in a distillation apparatus and mixed whilst stirring with 3.5 g 1-(tri-ethoxy-silyl)-propyl-3-methyl-imidazolium chloride. After stirring for 16 h at 95° C., the solvent was distilled off at 135° C. The solid was then extracted in a Soxhlet apparatus for 24 h with boiling $CH_2Cl_2$ and then dried under vacuum to remove any excess 1-(tri-ethoxy-silyl)-propyl-3-methyl-imidazolium chloride.

The CHN analysis (N: 3.28%; C: 12.82%; H: 3.50%) of the resultant functionalised support corresponds to 1.2 mmol imidazolium chloride per g. By ICP-AES analysis, the Si content was 29.76%.

1.2 g of the functionalised support was suspended at room temperature in 10 ml toluene in a Schlenk flask under a gas blanket. After adding 1.5 g $AlCl_3$ it was stirred for 16 h, then the solvent is removed under vacuum. The excess $AlCl_3$ was removed by 24 hour extraction with boiling $CH_2Cl_2$ to give an immobilised ionic liquid.

The CHN analysis (N: 3.28%; C: 12.82%; H: 3.50%) of the immobilised ionic liquid corresponds to 1.2 mmol imidazolium chloride per g and ICP-AES analysis (Si: 21.7%; Al: 11.06%) corresponds to 4.1 mmol $AlCl_3$ per g.

6.25 ml benzene (70 mmol) was alkylated with 1.5 ml (7 mmol) dodecene using 0.05 g of the immobilised ionic liquid as catalyst by heating the mixture with stirring for 1 hour to 40° C. in a Schlenk flask with reflux condenser. A 98.9% dodecene conversion was achieved with a selectivity of 99.5% monoalkylated product.

EXAMPLE 4

1.96 g (21 mmol) phenol was alkylated with 0.48 ml (2 mmol) dodecene using 0.14 g of the immobilised ionic liquid of Example 3 as catalyst by heating the mixture with stirring for 1 hour to 180° C. in a Schlenk flask with reflux condenser. A 62% dodecene conversion was achieved with a selectivity of 28% ether product (2-phenoxy dodecane) and 50% alkylation product (2-(4-hydroxyphenyl)dodecane).

EXAMPLE 5

1.54 g (12 mmol) naphthalene was alkylated with 1.33 ml (6 mmol) dodecene using 0.15 g of the immobilised ionic liquid of Example 3 as catalyst by heating the mixture with stirring for 1 hour to 80° C. in a Schlenk flask. A 96% dodecene conversion was achieved with a selectivity of 77% to the monoalkylated product.

EXAMPLE 6

1 g of the functionalised support from Example 3 was suspended at room temperature in toluene in a Schlenk flask under a gas blanket. 0.5 g $FeCl_3$ was added and the mixture stirred for 16 h and then the solvent is removed under vacuum. The excess $FeCl_3$ was removed by 24 hour extraction with boiling $CH_2Cl_2$ to give an immobilised ionic liquid.

The CHN analysis (N: 1.58%; C: 5.89%; H: 2.57%) corresponds to 0.56 mmol imidazolium chloride per g and the ICP-AES analysis(Si: 16.25%; Fe: 20.35%) corresponds to 3.6 mmol $FeCl_3$ per g.

4.9 ml (45 mmol) anisole, 0.85 ml (9 mmol) acetic anhydride and 0.1 g of the immobilised ionic liquid as catalyst were heated with stirring for 1 hour to 100° C. in a Schlenk flask with reflux condenser. The acetic anhydride conversion was 18.5% a selectivity of 98.4% to 4-methoxyacetophenone.

EXAMPLE 7

4.5 g of all-silica MCM 41 calcined at 500° C. was suspended in 50 ml toluene in a distillation apparatus and mixed whilst stirring with 3.6 g 1-(tri-ethoxy-silyl)-propyl-3-butyl-imidazolium chloride. The mixture was then stirred for 16 h at 95° C. and then the solvent was distilled off at 135° C. The solid was then extracted in a Soxhlet apparatus for 24 h with boiling $CH_2Cl_2$ and then dried under vacuum to remove any excess 1-tri-ethoxy-silyl)-propyl-3-butyl-imidazolium chloride.

The CHN analysis (N: 3.32%; C: 16.57%; H: 3.16%) of the resultant functionalised support corresponds to 1.2 mmol imidazolium chloride per g and the ICP-AES analysis gave a Si content of 34.54%.

3.0 g of the functionalised support were suspended at room temperature in 30 ml toluene in a Schlenk flask under a gas blanket. After adding 2.5 g $AlCl_3$, the mixture was stirred for 16 h and then the solvent was removed under vacuum. The excess $AlCl_3$ was removed by 24 hour extraction with boiling $CH_2Cl_2$ to give an immobilised ionic liquid.

Benzene was alkylated with dodecene in a steel reactor of 100 mm length and 6 mm diameter heated in a silicone oil bath to 40° C. using 0.4 g (12 mmol) of the immobilised ionic liquid as catalyst. A solution containing 41 g benzene and 9 g dodecene was pumped through the reactor at a WHSV of 7 $h^{-1}$. After a reaction time of 8 hours the catalyst still showed activity. A 88% dodecene conversion was achieved, with a 100% selectivity to the monoalkylated product.

EXAMPLE 8

A solution of 5.09 g of dodecylamine in 53 g of water and 41 g of ethanol was charged to a polypropylene vessel. 18.75 g (0.09 mol) of tetraethoxysilane and 3.19 g (0.01 mol) of 1-(4-triethoxysilyl)butyl-3-methyl-imidazolium chloride were added under vigorous stirring separately but simultaneously. The mixture was stirred for 18 h and then the resulting solid was filtered from the solution. Residual dodecylamine was then removed by Soxhlet extraction with ethanol for 24 h.

The CHN analysis (N: 2.8%; C: 12%; H: 2.73%) of the resultant functionalised support corresponds to 1 mmol imidazolium chloride per g.

4.0 g of the resultant functionalised support was suspended at room temperature in 40 ml toluene in a Schlenk flask under a gas blanket. After adding 3.0 g $AlCl_3$, the mixture was stirred for 16 h, then the solvent was removed under vacuum. The excess $AlCl_3$ was then is removed by 24 hour extraction with boiling $CH_2Cl_2$ to give the immobilised ionic liquid product.

The ICP-AES analysis (Si: 29.82%; Al: 4.74%) corresponds to 1.8 mmol $AlCl_3$ per g.

3.61 ml benzene (40 mmol) was alkylated with 0.9 ml (4 mmol) dodecene using 0.3 g of the immobilised ionic liquid as catalyst by heating the mixture with stirring for 1 hour to 80° C. in a Schlenk flask with reflux condenser. A 74% dodecene conversion was achieved with a selectivity of 82% to the monoalkylated product.

EXAMPLE 9

Under argon, 5 g of MCM 41 were stirred with a solution of 1 g $FeCl_3$ (6.3 mmol) in 30 ml methylene chloride for 1 hour at room temperature. Methylene chloride was subsequently evaporated under reduced pressure to give a treated support.

The treated support was stirred at room temperature with 2.5 g (6.7 mmol) of an ionic liquid consisting of butyl-methyl-imidazolium chloride and $FeCl_3$ in a molar ratio of 1:1.22 for three hours under inert gas. The formed supported ionic liquid was freed of excess ionic liquid by Soxhlet extraction with methylene chloride under reflux for a period of 24 hours. Methylene chloride was removed under vacuum to give the desired supported ionic liquid.

XRD spectra showed that the order/structure of the support did not deteriorate in this process.

By way of comparison when the above procedure was repeated, except that the treatment of the MCM 41 support with the $FeCl_3$ solution in methylene chloride was omitted, the XRD spectra of the supported ionic liquid obtained showed a severe deterioration of the support.

EXAMPLE 10

The process of Example 9 was repeated using ultra-stable Y-zeolite instead of MCM 41. XRD analysis of the fresh support and the formed supported ionic liquid showed that the support had not deteriorated in the process.

A coiled tubular reactor (diameter of the tube 6 mm, length 100 cm) with a frit near the downstream end carrying 1 g of the supported ionic liquid as a catalyst was placed in an oven. At a temperature of 150° C., and with a weight hourly space velocity (WHSV) of $4h^{-1}$, toluene was alkylated with 1-hexene. The process was conducted as a continuous gas phase reaction using a molar ratio of toluene to hexene of 10:1. The conversion, based on 1-hexene, dropped from 86% at the beginning of the reaction to around 45% after 3 hours. Thereafter, the conversion remained at the 45% level. A selectivity ranging from 65 to 85% was observed for the monoalkylated product. The other product was a mixture of hexene isomers and di-, or higher, alkylated products.

What is claimed is:

1. A process for preparing a supported ionic liquid having an organic cation and an anion, comprising attaching said organic cation to a solid support by covalent bonding, wherein said anion is a halide of an element selected from the group consisting of aluminium, gallium, iron, copper, zinc, indium, and tin.

2. The process of claim 1 wherein said organic cation is a quaternary ammonium, imidazolium or pyridinium ion.

3. The process of claim 1 wherein said ionic liquid is a liquid between −10° C. and 100° C. in the absence of a support.

4. The process of claim 1 wherein said ionic liquid is a liquid between −10° C. and 60° C. in the absence of a support.

5. The process of claim 1 wherein said solid support is a polymer.

6. The process of claim 1 wherein said solid support is an oxidic material.

7. The process according to claim 1 wherein said solid support is made by synthesizing the support in the presence of an organic compound that contains the cation of the ionic liquid or a precursor to said cation.

8. The process according to claim 1 wherein said attaching comprises contacting said solid support with an organic compound containing the cation of the ionic liquid, or a precursor to such a cation, wherein said organic compound has reactive groups that form covalent bonds with the support.

9. A process for preparing a composition comprising:
(i) forming a modified support material comprising:
a) a support material; and
b) a cation covalently bound to said support material; and
(ii) introducing to said cation a composition comprising an anion;
wherein said anion is a halide of an element selected from the group consisting of aluminium, gallium, iron, copper, zinc, indium, and tin; and
wherein the combination of said cation and said anion corresponds to that of an ionic liquid.

10. The process of claim 9 wherein said cation is an organic cation.

11. The process of claim 10 wherein said organic cation is a quaternary ammonium, imidazolium or pyridinium ion.

12. The process of claim 9 wherein said ionic liquid is a liquid between −10° C. and 100° C. in the absence of a support.

13. The process of claim 9 wherein said ionic liquid is a liquid between −10° C. and 60° C. in the absence of a support.

14. The process of claims 9 wherein said support material is a polymer.

15. The process of claim 9 wherein said support material is an oxidic material.

16. The process according to claim 9 wherein said support material is functionalized.

17. A process for preparing a composition comprising:
(i) forming a modified support material comprising:
a) a support material; and
b) a cation covalently bound to said support material;
(ii) simultaneously forming an anion which is a halide of an element selected from the group consisting of aluminium, gallium, iron, copper, zinc, indium, and tin,
wherein the combination of said cation and said anion corresponds to that of an ionic liquid.

18. The process of claim 17 wherein said cation is an organic cation.

19. The process of claim 18 wherein said organic cation is a quaternary ammonium, imidazolium or pyridinium ion.

20. The process of claim 17 wherein said ionic liquid is a liquid between −10° C. and 100° C. in the absence of a support.

21. The process of claim 17 wherein said ionic liquid is a liquid between −10° C. and 60° C. in the absence of a support.

22. The process of claims 17 wherein said support material is a polymer.

23. The process of claim 17 wherein said support material is an oxidic material.

24. The process according to claim 17 wherein said support material is functionalized.

25. A process for preparing a composition comprising:
(i) forming a functionalized support material comprising:
    a) a support material; and
    b) a cation or cation precursor covalently bound to said support material;
(ii) treating said functionalized support material with a composition comprising an anion or an anion precursor;
(iii) if said cation precursor is present, forming said cation; and
(iv) if said anion precursor is present, forming said anion;
wherein the combination of said cation and said anion corresponds to that of an ionic liquid and wherein said anion is a halide of an element selected from the group consisting of aluminium, gallium, iron, copper, zinc, indium, and tin.

26. The process of claim 25 wherein said cation is an organic cation.

27. The process of claim 26 wherein said organic cation is a quaternary ammonium, imidazalium or pyridinium ion.

28. The process of claim 25 wherein said ionic liquid is a liquid between −10° C. and 100° C. in the absence of a support.

29. The process of claim 25 wherein said ionic liquid is a liquid between −10° C. and 60° C. in the absence of a support.

30. The process of claim 25 wherein said support material is a polymer.

31. The process of claim 25 wherein said support material is an oxidic material.

32. The process according to claim 25 wherein said anion is formed by ion exchange of an inorganic halide with an anion precursor.

33. A process for preparing a composition comprising:
(i) forming in the absence of an ionic liquid, a functionalized support material comprising:
    a) a support material; and
    b) an anion or an anion precursor covalently bound to said support material;
(ii) treating said functionalized support material with a composition comprising a cation or a cation precursor;
(iii) if said cation precursor is present, forming said cation; and
(iv) if said anion precursor is present, forming said anion;
wherein the combination of said cation and said anion corresponds to that of an ionic liquid.

34. The process of claim 33 wherein said cation is an organic cation.

35. The process of claim 34 wherein said organic cation is a quaternary ammonium, imidazolium or pyridinium ion.

36. The process of claim 33 wherein said anion is an inorganic anion.

37. The process of claim 36 wherein said inorganic anion is a halide or a halide of an element selected from the group consisting of aluminium, antimony, gallium, iron, copper, zinc, indium, tin, boron and phosphorus.

38. The process of claim 33 wherein said ionic liquid is a liquid between −10° C. and 100° C. in the absence of a support.

39. The process of claim 33 wherein said ionic liquid is a liquid between −10° C. and 60° C. in the absence of a support.

40. The process of claim 33 wherein said support material is a polymer.

41. The process of claim 33 wherein said support material is an oxidic material.

42. A process for preparing an immobilised ionic liquid and composition comprising a cation, an anion and a support material, said cation and anion forming, in the absence of the support material, an ionic compound which is a liquid, and said cation being covalently bound to said support material, the process steps comprising:
(i) forming a functionalized support material comprising:
    a) a support material; and
    b) a cation or cation precursor covalently bound to said support material;
(ii) treating said functionalized support material with an ionic liquid comprising an anion; and
(iii) if said cation precursor is present, forming said cation,
wherein said anion is a halide of an element selected from the group consisting of aluminium, gallium, iron, copper, zinc, indium, and tin.

43. The process of claim 42 wherein said cation is an organic cation.

44. The process of claim 43 wherein said organic cation is a quaternary ammonium, imidazolium or pyndinium ion.

45. The process of claim 42 wherein said ionic liquid is a liquid between −10° C. and 100° C. in the absence of a support.

46. The process of claim 42 wherein said ionic liquid is a liquid between −10° C. and 60° C. in the absence of a support.

47. The process of claim 42 wherein said support material is a polymer.

48. The process of claim 42 wherein said support material is an oxidic material.

49. A process for preparing a composition comprising:
(i) forming in the absence of an ionic liquid, a functionalized support material comprising:
    a) a support material; and
    b) an anion or an anion precursor covalently bound to said support material;
(ii) thereafter treating said functionalized support material with an ionic liquid comprising a cation;
(iii) if said anion precursor is present, forming said anion;
wherein the combination of said cation and said anion corresponds to that of an ionic liquid.

50. The process of claim 49 wherein said cation is an organic cation.

51. The process of claim 50 wherein said organic cation is a quaternary ammonium, imidazolium or pyndinium ion.

52. The process of claim 49 wherein said anion is an inorganic anion.

53. The process of claim 52 wherein said inorganic anion is a halide or a halide of an element selected from the group consisting of aluminium, antimony, gallium, iron, copper, zinc, indium, tin, boron and phosphorus.

54. The process of claim 49 wherein said ionic liquid is a liquid between −10° C. and 100° C. in the absence of a support.

55. The process of claim 49 wherein said ionic liquid is a liquid between −10° C. and 60° C. in the absence of a support.

56. The process of claim 49 wherein said support material is a polymer.

57. The process of claim 49 wherein said support material is an oxidic material.

58. A composition comprising:
 a) a solid support material;
 b) a cation covalently bonded to said solid support material; and
 c) an anion which is a halide of an element selected from the group consisting of aluminium, gallium, iron, copper, zinc, indium, and tin,
 wherein an ionic compound formed from said cation and said anion would be a liquid in the absence of a support.

59. The composition of claim 58 wherein said cation is an organic cation.

60. The composition of claim 59 wherein said organic cation is a quaternary ammonium ion.

61. The composition of claim 58 wherein said ionic liquid is a liquid between −10° C. and 100° C. in the absence of a support.

62. The composition of claim 58 wherein said ionic liquid is a liquid between −10° C. and 60° C. in the absence of a support.

63. The composition of claim 58 wherein said support material is a polymer.

64. The composition of claim 58 wherein said support material is an oxidic material.

65. The composition of claim 58 further comprising at least one transition metal compound or complex.

66. The composition of claim 63 wherein said polymer comprises the cations of the ionic liquid.

67. The composition of claim 59 wherein said organic cation is an imidazolium ion.

68. The composition of claim 59 wherein said organic cation is an pyridinium ion.

69. The composition of claim 65 wherein said transition metal compound or complex is a noble metal compound or complex.

* * * * *